(12) United States Patent
Boese et al.

(10) Patent No.: US 7,801,342 B2
(45) Date of Patent: Sep. 21, 2010

(54) METHOD FOR DETERMINING THE POSITION AND ORIENTATION OF AN OBJECT, ESPECIALLY OF A CATHETER, FROM TWO-DIMENSIONAL X-RAY IMAGES

(75) Inventors: Jan Boese, Eckental (DE); Norbert Rahn, Forchheim (DE); Bernhard Sandkamp, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1128 days.

(21) Appl. No.: 11/471,123

(22) Filed: Jun. 20, 2006

(65) Prior Publication Data
US 2006/0285638 A1 Dec. 21, 2006

(30) Foreign Application Priority Data
Jun. 21, 2005 (DE) .................... 10 2005 028 746

(51) Int. Cl.
*G06K 9/00* (2006.01)
*G01N 23/04* (2006.01)
*A61B 5/05* (2006.01)

(52) U.S. Cl. .................. 382/128; 382/132; 382/154; 378/62; 378/63; 600/424

(58) Field of Classification Search .......... 382/128, 382/132, 154; 600/425, 407, 424; 378/21, 378/62, 64, 63
See application file for complete search history.

(56) References Cited

U.S. PATENT DOCUMENTS

| | | | |
|---|---|---|---|
| 6,096,050 A | 8/2000 | Audette | |
| 6,226,546 B1 * | 5/2001 | Evans | 600/424 |
| 6,493,575 B1 * | 12/2002 | Kesten et al. | 600/431 |
| 6,587,709 B2 * | 7/2003 | Solf et al. | 600/424 |
| 6,674,916 B1 | 1/2004 | Deman et al. | |
| 7,190,819 B2 * | 3/2007 | Viswanathan | 382/128 |
| 7,197,354 B2 * | 3/2007 | Sobe | 600/424 |
| 7,603,159 B2 * | 10/2009 | Rasche | 600/424 |
| 7,650,178 B2 * | 1/2010 | Scheffler | 600/424 |
| 2001/0039421 A1 | 11/2001 | Heilbrun et al. | |

(Continued)

FOREIGN PATENT DOCUMENTS

DE 102 10 646 A1 10/2003

(Continued)

OTHER PUBLICATIONS

Meyers et al, Registration of Three-Dimensional Cardiac Catheter Models to Single-Plane fluoroscopic Images, IEEE Transactions on Biomedical Engineering, vol. 46, No. 12, Dec. 1999.*

(Continued)

*Primary Examiner*—Vu Le
*Assistant Examiner*—Andrae S Allison

(57) ABSTRACT

To determine the position and orientation of an object in a x-ray image the x-ray image is initially pre-processed. A three-dimensional template (data record) of the object based on the known constructional features of the object is created. Three parameters for the position and for the orientation respectively are modified iteratively. The three-dimensional template with the parameters for position and orientation is projected in each case onto a two-dimensional plane and the created image is compared on the basis of the generation of a degree of similarity with the pre-processed x-ray image.

11 Claims, 2 Drawing Sheets

U.S. PATENT DOCUMENTS

| | | |
|---|---|---|
| 2003/0060700 A1* | 3/2003 | Solf et al. .................. 600/411 |
| 2003/0181809 A1 | 9/2003 | Hall et al. |
| 2005/0015006 A1 | 1/2005 | Mitschke et al. |
| 2005/0038338 A1 | 2/2005 | Bono et al. |
| 2006/0182224 A1* | 8/2006 | Besson ..................... 378/146 |

FOREIGN PATENT DOCUMENTS

| | | |
|---|---|---|
| DE | 697 18 486 T2 | 10/2003 |
| DE | 103 25 003 A1 | 12/2004 |
| EP | 0 474 307 B1 | 5/2000 |
| EP | 0 894 473 B1 | 11/2003 |

OTHER PUBLICATIONS

Fallavollita et al , Fluoroscopic navigation to guide RF catheter ablation of cardiac arrhythmias, Proceedings of the 26th Annual International Conference of the IEEE EMBS San Francisco, CA, USA • Sep. 1-5, 2004.* de Boer et al., "3D-Lokalisation von Elektroden auf und in dem menschlichen Körper ausgehend von biplanaren Röntgenaufnahmen", Biomedizinische Technik, Sep. 1998, pp. 474-475, vol. 43-1.

de Boer et al., "Methods for determination of electrode positions in tomographic images", International Journal of Bioelectromagnetism, Sep. 2000, pp. 1-35, No. 2, vol. 2.

de Boer et al., "Ein modellbasierter Ansatz zur Lokalisation von Basket-Kathetern füar endokardiales Mapping", Biomedizinische Technik, Sep. 2000, pp. 57-58, vol. 45-1.

Kalman, "A new approach to linear filtering and prediction problems", Trans. ASME, J. Basic Eng. Series 82D, Mar. 1960, pp. 35-45.

Rink et al., "Recovery of the 3-D location and motion of a rigid object through camera image (An Extended Kalman Filter Approach)", International Journal of Computer Vision, Apr. 1989, pp. 373-394, Heft vol. 2, No. 4.

* cited by examiner

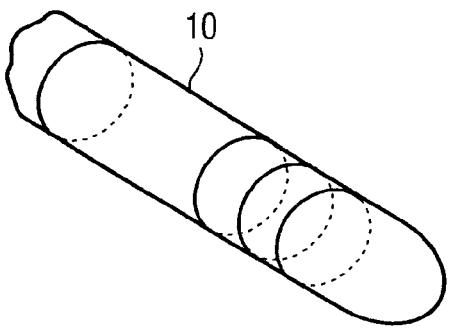
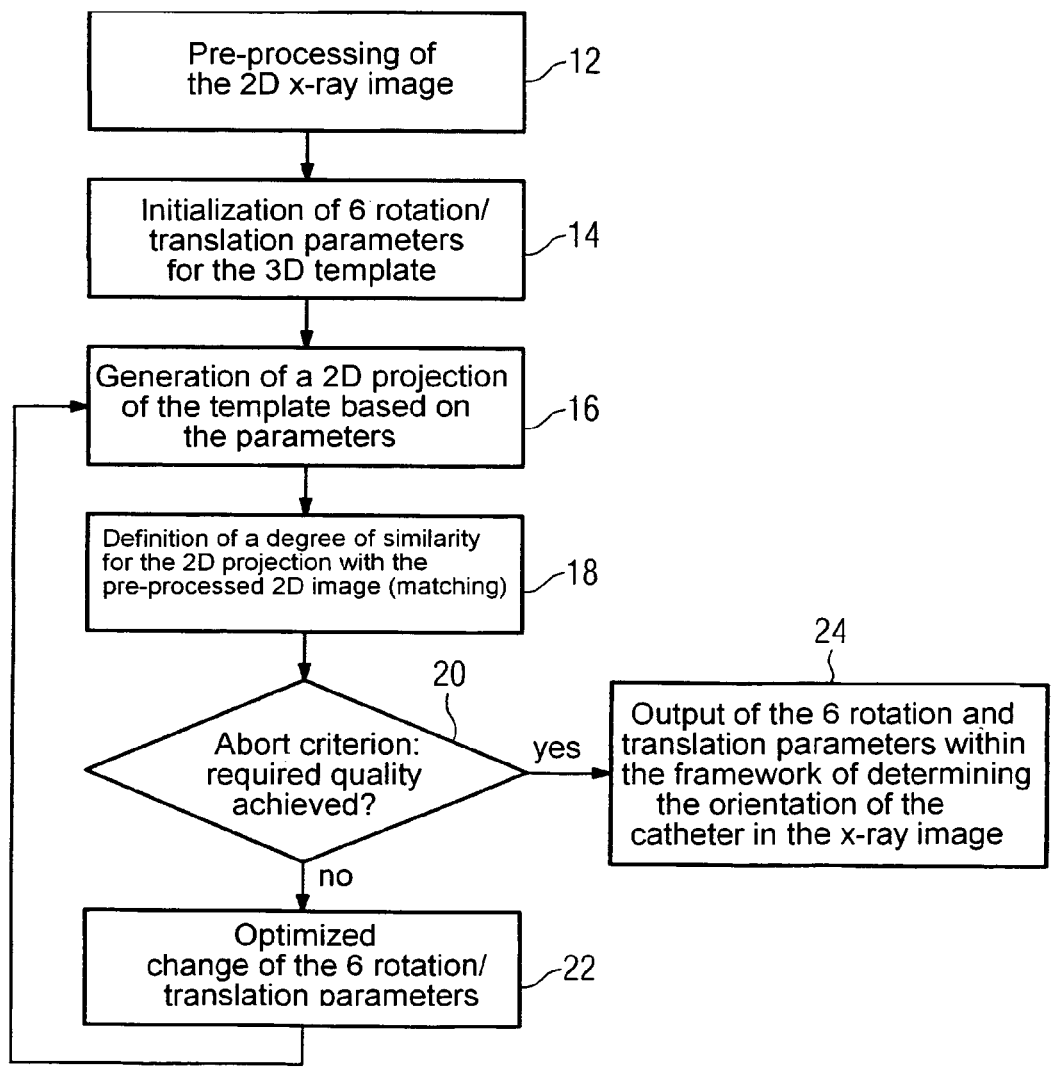

METHOD FOR DETERMINING THE POSITION AND ORIENTATION OF AN OBJECT, ESPECIALLY OF A CATHETER, FROM TWO-DIMENSIONAL X-RAY IMAGES

CROSS REFERENCE TO RELATED APPLICATIONS

This application claims the benefits of German Patent application No. 10 2005 028 746.8 filed Jun. 21, 2005 and is incorporated by reference herein in its entirety.

FIELD OF THE INVENTION

The invention relates to a method for automatically determining the position and orientation of an object, especially such as a catheter, from two-dimensional x-ray images. The determination can include identifying the position and the orientation of the object in the x-ray image. Determining the position and the orientation can also include a subsequent localization of the object in the three-dimensional space.

BACKGROUND OF THE INVENTION

In numerous interventions in a patient, instruments, especially catheters are introduced into the body. In addition to interventional radiological and electrophysiological procedures, these procedures also include neurological interventions or interventions in the abdominal area (at the liver or kidneys or gall bladder). As a matter of routine the position of the instrument introduced is monitored during such interventions by an x-ray system, that is by a monoplanar or biplanar system, which monitors the position of the instrument or the catheter which has been introduced. There is an increasing demand, as well as simply representing the instrument on a screen, to automatically determine its three-dimensional position and orientation. Then for example the three-dimensional position and the orientation of the instrument can be displayed on previously recorded three-dimensional image data, e.g. on a CT or a three-dimensional angiography. With electrophysiological methods too an automatic localization of objects is desirable for generating so-called electrophysiological maps.

Previously electroanatomical mapping systems (e.g. the CARTO system produced by Biosense Webster, Diamondbar, Calif., USA) have been used for three-dimensional real time localization of catheters during electrophysiological procedures. Special catheters with 6D position or orientation sensors are used in this product. The disadvantage of this is that only the special catheters can be localized and three-dimensionally visualized. The use of these catheters is also particularly associated with high costs.

In principle the three-dimensional localization of instruments using image data by detecting the instrument or a characteristic point in one or more images is also known. The 3D position can thus be determined using back projection from two x-ray images which are recorded from different directions for example.

SUMMARY OF THE INVENTION

The object of the present invention is to provide a method for determining the position and orientation of an object, which operates more simply compared to the prior art, and on the other hand is especially reliable.

This object is achieved by a method in accordance with the claims and an x-ray imaging system in accordance with the claims.

Accordingly the inventive method comprises the following steps:
a) Generation of a first x-ray image and pre-processing of the x-ray image for high-lighting imaging structures of the object in the x-ray image,
b) Generation of a three-dimensional template for the object based on the known technical characteristics of the object (e.g. from constructional drawings),
c) Initialization of three parameters in each case for the position and for the orientation of the template in the 3D area,
d) Generation of a two-dimensional projection of the template with reference to the six parameters for position and orientation of the object,
e) Comparison of the two-dimensional projection with the pre-processed x-ray image and determination of a degree of similarity,
f1) If the degree of similarity justifies aborting the procedure: Use of the current six parameters to determine (define) position and orientation of the object relative to the x-ray image,
f2) If the degree of similarity is not sufficiently good: Adapting the set of six parameters and repeating steps d) and e) in an optimization loop until the degree of similarity justifies aborting the procedure.

A template is thus used in the invention which records the structures which are usually visible in x-ray images. Such a template is a three-dimensional data record which adapts to the form and structure of the object, especially its meta parts. Unlike many procedures in the prior art, in which only any unusual structure which differs in any way from bones etc also shown in the x-ray image is evaluated as a recognized structure, the invention uses as the starting point the specification of that which an automatic computer recognition is able to detect in a (pre-processed) x-ray image. This is simplified by the pre-processing of the x-ray image, for example the x-ray image can be subjected to a highpass filter or even completely converted into binary, i.e. become an image with just black or white on which particularly sharp structures are especially easy to see after the highpass has been run.

Starting from the template, i.e. that which is to be detected on the image, the invention now determines the position and orientation of the object as it is to be seen in the preprocessed x-ray image. This is done iteratively.

Matching is performed in each case, i.e. a two-dimensional projection of the template is compared with the pre-processed x-ray image and a degree of similarity is determined. There are normal similarity metrics available in the prior art (mutual information, correlation etc.) for this degree of similarity. The degree of similarity is a measure of quality for the match. With iterations, depending on the measure used the aim is to produce a maximum of a minimum. Normal methods are available for such iterations. For example when the parameters are changed, the translation parameters can be changed to start with and then the rotation parameters can be changed etc.

In a preferred embodiment the entire inventive method is also executed for a second x-ray image. A new set of six parameters for position and orientation of the object in the second (pre-processed) x-ray image is thus determined. In determining the six (new) parameters, the set can also take account of the six parameters obtained on the basis of the first x-ray image.

On the basis of the projection parameters known from the calibration of the x-ray system a back projection of the object from the relevant x-ray image into the three-dimensional area can be executed. Because of an uncertainty in the parameter which describes the depth which occurs almost fundamentally the object is not localized precisely enough by the matching with the template in the three-dimensional area but instead a projection line is obtained.

Such a projection line can on the one hand be projected in its turn onto the second x-ray image so that to obtain the six parameters on the basis of the second x-ray image only the environment of the projection line has to be taken into account, saving much time and computing effort.

It is also possible to compute such a projection line on the basis of the second x-ray image. Two projection lines are then obtained, which in the ideal case intersect within the space. In a preferred version of the method the point of least distance to the projection lines is determined. This point is used for localization of the object in the three-dimensional space. The smallest distance can be determined in the usual way with a quadratic procedure, with the sum of the quadratics of the two distances to the relevant projection lines having to be minimized.

The smallest distance of the two projection lines from each other is used as a measure for the quality of the localization of the object. If the localization is perfect the two projection lines intersect, i.e. the smallest distance is zero.

Thus, in accordance with a preferred embodiment, we have expanded the method for determining the position and orientation from a method in which six parameters are determined which specify the position and orientation of the object in the x-ray image in such a way that the object is localized in the three-dimensional space.

The inventive method can be further expanded. Thus a previous assumption was that the template reflected an object which remained rigid. With a catheter parts behind the tip especially are also bendable. These can also be included. The template must then be divided into a part of the object which remains rigid and a bendable part of the object. The overall progress of the object can be represented by the use of support points and interpolation between them by way of a model. In other words further parameters can be incorporated into the optimization loop which record the bending of the object in some form or other. For the sake of simplicity it is best to determine the position and orientation of the part of the object which remains rigid on the basis of the six parameters, with the bending of the object being described by further parameters.

The invention thus also comprises an x-ray imaging system. A modem x-ray imaging system comprises an x-ray device and a computer, (a data processing unit). A new aspect of the invention is that a three-dimensional data record relating to the contours of a construction-related known object, such as a catheter in particular, is stored in the computer. Preferably the computer is designed to execute the steps of defining parameters for the position and the orientation of the object in the pre-processed x-ray image, creating a two-dimensional projection of the template on the basis of the six parameters, matching of the two-dimensional projection to the pre-processed x-ray image.

BRIEF DESCRIPTION OF THE DRAWINGS

A preferred embodiment of the invention will now be described with reference to the drawing, in which:

FIG. 1 shows a schematic diagram of a template for a normal catheter,

FIG. 2 shows the steps of the method in accordance with invention, and

DETAILED DESCRIPTION OF THE INVENTION

Figure 3:
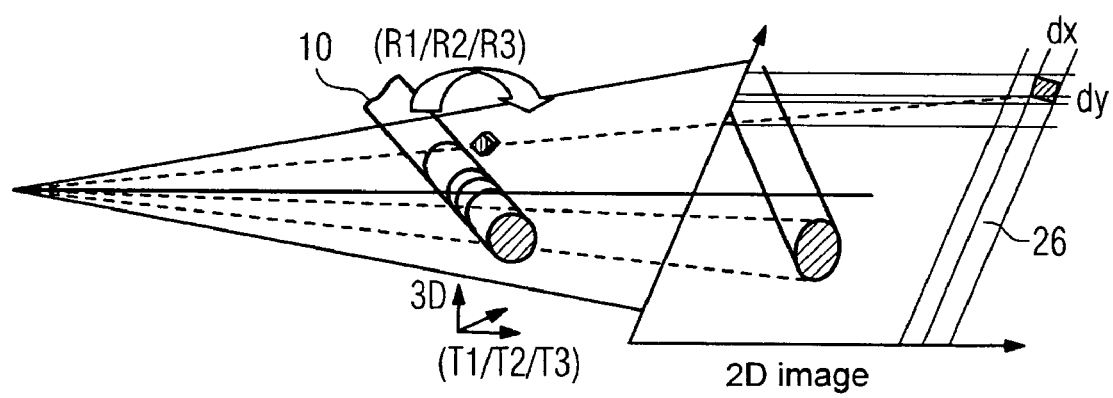
FIG. 3 represents the projection of the three-dimensional templates from FIG. 1 on a two-dimensional plane.

To enable a catheter to be automatically detected in an x-ray image, the computer system is notified of the type of structures to be expected in the image. Instead of storing a plurality of projections of such catheters in x-ray images, a three-dimensional image of one catheter is stored. A three-dimensional template shown in FIG. 1 of a catheter 10 in particular shows the metallic structures of the catheter at the tip of this device. A catheter essentially consists of a plastic tube which is 3-4 mm thick and a metal cap on the tip which projects by around four to eight millimeters. The template shown in FIG. 1 shows this metal tip in particular.

For an intervention, for example an electrophysiological investigation of the heart, a catheter is introduced into the patient's body. This is undertaken as usual under x-ray control, i.e. x-ray images are continuously recorded on which the catheter can be detected. The present invention deals with determining the position and the orientation of the catheter in the image by a computer system.

To this end, the computer system must have a generated two-dimensional x-ray image available to it. This x-ray image is pre-processed, namely especially subjected to highpass filtering. The highpass is used to accentuate the structures especially sharply and especially strongly so that the sharp-edged part structures of the catheter are presented particularly clearly (FIG. 2, step 12). As part of the pre-processing of the two-dimensional x-ray image a binary image can also be generated. A binary image is an image in which the individual image elements are merely assigned a logical one or a logical zero so that the image can be presented in black-and-white without grey shades. The template shown in FIG. 1 is suitable for use of such a binary image.

Six rotation or transformation parameters for the 3D template are now initialized in step 14.

The reader is referred to FIG. 3 for an explanation of why six rotational translation parameters are involved in the calculation. The position of the template 10 is determined by three degrees of freedom in FIG. 3, namely by a corresponding displacement of the template 10 along three axes at right angles to each other (translation parameters T1, T2 and T3). The orientation of the template 10 can be described with reference to the rotation around three axes at right angles to each other, namely by the angles of rotation R1, R2 and R3.

In addition to these six degrees of freedom the five intrinsic degrees of freedom of the imaging system (it's the projection geometry) also have a role to play in the projection of the template onto a two-dimensional image 26. A projection matrix P is produced as $$P = K_{intrinsic} \times T_{extrinsic}.$$

The matrix $K_{intrinsic}$ describes the five intrinsic degrees of freedom of the imaging system (essentially the projection geometry of the imaging system) and the matrix $T_{extrinsic}$ describes the six degrees of freedom relating to position and orientation. The five intrinsic degrees of freedom of the imaging system are now deemed to be known, they can be determined for example by system calibration at the x-ray C-arm. For uniquely determining the projection the above-mentioned six parameters for definition of the six degrees of freedom of the matrix $T_{extrinsic}$ are thus required.

It is now possible in step 16 (FIG. 2) to generate such a two-dimensional projection of the template on the basis of the parameters. The two-dimensional image 26 shown in FIG. 3 represents such a two-dimensional projection of the template. In step 18 the two-dimensional projection is now matched to the pre-processed two-dimensional x-ray image. In other words a degree of similarity for the two-dimensional projection is defined. It must be clarified whether the parameters T1, T2, T3, R1, R2 and R3 are sufficiently well selected so that they reflect the real situation. On the basis of the degree of similarity an abort criterion is now determined in step 20 to indicate whether the required quality has been reached. As a rule this is not the case in the first instance. The six rotation and translation parameters are then modified in step 22 and there is a return to steps 16, and steps 16, 18 and 20 are repeatedly executed again. This loop from steps 16 through 22 is repeated until such time as the required quality of the degree of similarity is obtained. As a rule such a degree of similarity is defined so that the six parameters best match the reality when the degree of similarity is at its maximum.

If the maximum degree of similarity is initially approximately determined, i.e. a required quality is achieved (e.g. also by undershooting a threshold value) the six rotation and translation parameters are output within the framework of determining position and orientation of the catheter in the x-ray image. They can for example be displayed to the electrophysiologist or also continue to be used within the computer system. In the ideal case six parameters T1, T2, T3, R1, R2, R3, which reflect the real position of the catheter should have been obtained using the previous method. In other words FIG. 3 represents the situation in model form in which the x-ray image was taken, with the corresponding positioning and distortions and displacements etc. of the catheter being described by the parameters. The real catheter is thus located with the same translation and rotation in the body of a patient.

With an advanced embodiment the actual calculation takes account of the fact that, with the displacement of the template or of the real catheter along the axis of projection only a slight change in size in the two-dimensional image occurs so that the translation parameter which reflects this depths is not sufficiently precise. Since only five of the six degrees of freedom are thus recorded precisely, a back projection is generated from the two-dimensional image and a projection line is obtained which runs from the detected position to be projection center. From another recording angle a second x-ray image is created and such a projection line is also obtained. The point at which the projection lines of the two x-ray images come especially close to each other in the three-dimensional space or where they intersect if necessary is where the catheter can be localized in the three-dimensional space. In other words the relevant x-ray images provide five of the six degrees of freedom precisely and two x-ray images are used to define the sixth degree of freedom. The recording of a second x-ray image not shown in the Figure is especially sensible because the catheter position and orientation is in many images not reliable as a result of the imaging of bones etc. In other words the maximum degree of similarity does not always produce the correct result with many images. Then, if symptoms are present, the six rotation and translation parameters can be used as a starting point for the first x-ray image with a projection line which is produced with reference to these parameters able to be projected into the second x-ray image. A search is then made in the environment of the projection line for a sub-maximum of the degree of similarity whereby the real parameters can possibly also be found. With disturbance structures in the image the overall structures can be namely so designed that the degree of similarity for correct "definition" of the six parameters does not produce the maximum but merely a sub-maximum.

The invention is naturally also applicable to systems and methods in which a plurality of x-ray images are taken consecutively. During electrophysiological interventions in which a catheter is inserted the insertion of the catheter can be continuously monitored by generating x-ray images. For an initial execution of the inventive method described with reference to FIG. 2, six rotation and translation parameters are obtained which can be included as the starting point for those parameters which are generated from subsequent x-ray images. Because of plausibility checks not much can change for example in the translation or the rotation. This then saves on computing time in subsequent images.

The detected catheter position or orientation can then be shown in color in the current two-dimensional x-ray images, for example as an arrow.

The use of the template has the advantage that the detection of new catheters coming onto the market does not require new software to be developed for catheter detection but merely a new catheter-specific three-dimensional template to be added into a template database. With advanced systems an automatic template selection from the template database is possible. The method can also be used during interventions in which a number of instruments must be localized.

The invention claimed is:

1. A method for determining a three-dimensional position and angular orientation of a catheter from two-dimensional x-ray images, comprising:
   a) generating a first x-ray image;
   b) pre-processing the first x-ray image to accentuate the imaging structures of the catheter in the x-ray image;
   c) generating a three-dimensional template for the catheter based on known dimensional characteristics of the catheter;
   d) initializing three parameters for the position and three parameters for the angular orientation of the catheter relative to the pre-processed x-ray image;
   e) generating, by a data processing unit, a two-dimensional projection of the template with reference to the six parameters for position and angular orientation of the catheter;
   f) comparing, by a data processing unit, the two-dimensional projection with the pre-processed x-ray image;
   g) determining, by a data processing unit, a similarity between the two-dimensional projection and the pre-processed x-ray image based on the comparison;
   h) aborting, by a data processing unit, the procedure if the similarity exceeds a predetermined threshold and establishing the initialized position and orientation parameters as the actual position and orientation of the catheter in the x-ray image;
   i) repeating steps e) through h) in an optimization loop until the degree of similarity exceeds a predetermined threshold,
   j) obtaining, by a data processing unit, a first projection line based on the six position and orientation parameters obtained with the first x-ray image via a back-projection of the catheter from the first x-ray image into the three-dimensional space;
   k) obtaining, by a data processing unit, a second projection line based on the six position and orientation parameters based on the second x-ray image via a back-projection of the object from the second x-ray image into the three-dimensional space;
   l) determining, by a data processing unit, the location with the smallest quadratic distance to the two projection lines; and
   m) determining, by a data processing unit, an intersection point that locates the catheter in three-dimensional space.

2. The method in accordance with claim 1, wherein the three parameters for the position of the catheter correspond to the three translational degrees of freedom of the catheter and the three parameters for the angular orientation of the catheter correspond to the three rotational degrees of freedom of the catheter.

3. The method in accordance with claim 1, wherein the pre-processing of the first x-ray image comprises high-pass filtering or conversion of the x-ray image into binary format.

4. The method in accordance with claim 1, further comprising the step of:
   generating a second x-ray image from a different recording angle than the first x-ray image,
   pre-processing the second x-ray image for accentuating the imaging structures of the catheter object in the second x-ray image, and
   further analyzing the second x-ray image in accordance with steps d) through i).

5. The method in accordance with claim 3, wherein the six position and orientation parameters based on the first x-ray image are considered in the determination of the six new position and orientation parameters associated with the second x-ray image.

6. The method in accordance with claim 1, wherein the smallest distance between the two projection lines is used as a measure of the quality of the location determination of the catheter.

7. The method in accordance with claim 1, wherein the three-dimensional template:
   identifies a part of the catheter that remains rigid and a part that can be bent,
   identifies further parameters that record the bending of the object, and
   including the further identified parameters in the optimization loop of steps d) through i).

8. An X-ray imaging system comprising:
   an x-ray device for providing x-ray images including a first x-ray image, the first x-ray image is pre-processed to accentuate the imaging structures of the catheter in the x-ray image;
   a data processing unit that stores a three-dimensional data record of contours of a catheter to be automatically detected from the x-ray images, wherein the data processing unit:
   a) initializes three parameters for the position and three parameters for the angular orientation of the catheter relative to the pre-processed x-ray image;
   b) generates a two-dimensional projection of the template with reference to the six parameters for position and angular orientation of the catheter;
   c) compares the two-dimensional projection with the pre-processed x-ray image;
   d) determines a similarity between the two-dimensional projection and the pre-processed x-ray image based on the comparison;
   e) aborts the procedure if the similarity exceeds a predetermined threshold and establishing the initialized position and orientation parameters as the actual position and orientation of the catheter in the x-ray image; and
   f) repeats steps b) through e) in an optimization loop until the degree of similarity exceeds a predetermined threshold
   g) obtaining a first projection line based on the six position and orientation parameters obtained with the first x-ray image via a back-projection of the catheter from the first x-ray image into the three-dimensional space;
   h) obtaining a second projection line based on the six position and orientation parameters based on the second x-ray image via a back-projection of the object from the second x-ray image into the three-dimensional space;
   i) determining the location with the smallest quadratic distance to the two projection lines; and
   j) determining an intersection point that locates the catheter in three-dimensional space.

9. The imaging system in accordance with claim 8, wherein the three parameters for the position of the catheter correspond to the three translational degrees of freedom of the catheter and the three parameters for the angular orientation of the catheter correspond to the three rotational degrees of freedom of the catheter.

10. The imaging system in accordance with claim 8, wherein the pre-processing of the first x-ray image comprises high-pass filtering or conversion of the x-ray image into binary format.

11. The imaging system in accordance with claim 8, wherein the data processing unit further comprises:
   generating a second x-ray image from a different recording angle than the first x-ray image,
   pre-processing the second x-ray image for accentuating the imaging structures of the catheter object in the second x-ray image, and
   further analyzing the second x-ray image in accordance with steps a) through f).

* * * * *